US011092591B2

(12) United States Patent
Golden et al.

(10) Patent No.: US 11,092,591 B2
(45) Date of Patent: Aug. 17, 2021

(54) HOST AND INTESTINAL MICROBIOTA DERIVED METABOLOMIC BLOOD PLASMA SIGNATURE FOR PRIOR RADIATION INJURY

(71) Applicant: ALBERT EINSTEIN COLLEGE OF MEDICINE, Bronx, NY (US)

(72) Inventors: Aaron Alain-Jon Golden, Rye, NY (US); Pilib Ó Broin, Bronx, NY (US); Chandan Guha, Scarsdale, NY (US); Irwin Kurland, Lloyd Harbor, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/518,284

(22) PCT Filed: Nov. 13, 2015

(86) PCT No.: PCT/US2015/060517
§ 371 (c)(1),
(2) Date: Apr. 11, 2017

(87) PCT Pub. No.: WO2016/081292
PCT Pub. Date: May 26, 2016

(65) Prior Publication Data
US 2017/0299573 A1 Oct. 19, 2017

Related U.S. Application Data

(60) Provisional application No. 62/082,781, filed on Nov. 21, 2014.

(51) Int. Cl.
*G01N 33/49* (2006.01)
*G01T 1/04* (2006.01)
(Continued)

(52) U.S. Cl.
CPC .......... *G01N 33/492* (2013.01); *G01N 30/72* (2013.01); *G01N 30/88* (2013.01);
(Continued)

(58) Field of Classification Search
None
See application file for complete search history.

(56) References Cited

U.S. PATENT DOCUMENTS 8,269,163 B2 * 9/2012 Pevsner ............. G01N 33/6893
250/282
2008/0128608 A1 * 6/2008 Northen ............. H01J 49/0413
250/282

(Continued)

FOREIGN PATENT DOCUMENTS

WO 2009137015 A2 11/2009
WO WO 2009137015 A2 * 11/2009
(Continued)

OTHER PUBLICATIONS

PCT International Search Report and Written Opinion, dated Mar. 6, 2016 in connection with PCT International Application No. PCT/US2015/60517, 12 pages.
(Continued)

*Primary Examiner* — Andrew Smyth
(74) *Attorney, Agent, or Firm* — Perkins Coie LLP

(57) ABSTRACT

Provided are methods of determining prior radiation dose exposure levels for subjects, and kits therefor. Also provided are methods of treatment.

11 Claims, 4 Drawing Sheets

(51) Int. Cl.
*G01N 30/72* (2006.01)
*G01N 33/68* (2006.01)
*G01N 30/88* (2006.01)

(52) U.S. Cl.
CPC ..... *G01N 33/6848* (2013.01); *G01N 33/6893* (2013.01); *G01T 1/04* (2013.01); *G01N 2030/8813* (2013.01); *G01N 2570/00* (2013.01); *G01N 2800/40* (2013.01)

(56) References Cited

U.S. PATENT DOCUMENTS

| | | | | |
|---|---|---|---|---|
| 2009/0318556 | A1* | 12/2009 | Idle | C07D 473/04 |
| | | | | 514/562 |
| 2013/0052172 | A1* | 2/2013 | Baker | C12Q 1/689 |
| | | | | 424/93.45 |
| 2014/0024132 | A1* | 1/2014 | Jia | G01N 33/5088 |
| | | | | 436/173 |
| 2014/0343865 | A1* | 11/2014 | Brown | G16B 5/00 |
| | | | | 702/19 |

FOREIGN PATENT DOCUMENTS

| | | | | |
|---|---|---|---|---|
| WO | 2013086365 A2 | | 2/2013 | |
| WO | WO 2013086365 A2 * | 6/2013 | ......... | G01N 33/5011 |
| WO | WO-2013086365 A2 * | 6/2013 | ....... | G01N 33/57438 |
| WO | WO 2013086365 A8 * | 5/2014 | ......... | G01N 33/5011 |
| WO | WO-2013086365 A8 * | 5/2014 | ......... | G01N 33/5011 |
| WO | WO 2013086365 A3 * | 7/2014 | ......... | G01N 33/5011 |
| WO | WO-2013086365 A3 * | 7/2014 | .............. | A61P 13/12 |

OTHER PUBLICATIONS

Xi B et al., entitled "Statistical analysis and modeling of mass spectrometry-based metabolomics data," Methods in Molecular Biology, Aug. 14, 2014, vol. 1198, pp. 333-353.

Broin P O et al., entitled "Intestinal Microbiota-Derived Metabolomic Blood Plasma Markers for Prior Radiation Injury,", International Journal of Radiation Oncology Biology Physics, Jun. 1, 2015, vol. 91, No. 2, pp. 360-367.

* cited by examiner

HOST AND INTESTINAL MICROBIOTA DERIVED METABOLOMIC BLOOD PLASMA SIGNATURE FOR PRIOR RADIATION INJURY

CROSS-REFERENCE TO RELATED APPLICATIONS

This application is a U.S. national stage entry under 35 U.S.C. § 371 of PCT International Patent Application No. PCT/US2015/060517, filed Nov. 13, 2015, which claims benefit of U.S. Provisional Application No. 62/082,781, filed Nov. 21, 2014, the contents of each of which are incorporated herein by reference into the subject application.

STATEMENT OF GOVERNMENT SUPPORT

This invention was made with government support under grant number AI091175 awarded by the National Institutes of Health. The government has certain rights in the invention.

BACKGROUND OF THE INVENTION

Throughout this application various publications are referred to in square brackets. Full citations for these references may be found at the end of the specification. The disclosures of these publications, and all patents, patent application publications and books referred to herein, are hereby incorporated by reference in their entirety into the subject application to more fully describe the art to which the subject invention pertains.

The ability to accurately discern the received whole-body radiation dose after a specific radiological event is of great relevance to the subsequent triaging of victims for treatment. Ionizing radiation induces a diversity of cellular responses across a range of tissue types and these all contribute towards an overall clinical diagnosis which has been to date traditionally classified as acute, late consequential or late [1]. The most serious of these, acute radiation syndrome (ARS), need to be identified as soon as possible so as to ensure patients can be offered appropriate and immediate medical attention, with treatments specifically designed to ameliorate the worst effects of radiation sickness [2].

The study of metabolites and lipids in biofluids such as urine or blood plasma represents a particularly attractive mechanism whereby the holistic, whole-body response to radiation may be monitored. Whilst the presence of specific gene transcripts (and to a lesser extent proteins) is tightly coupled to their tissue types of origin, metabolites represent the effective endpoints of cellular regulatory processes [3]. As such, the presence and concentration of specific metabolites are likely to be a direct consequence of the whole-body response to any perturbations, such as those from ionizing radiation. Easy to obtain, prepare and subsequently process, the isolation of such metabolites is also in many ways much less complex than the more rigorous laboratory controlled environments needed to extract and process nucleic acids or proteins, offering a potentially effective technological development pathway for an ultimately deployable 'kit' in the field.

Several previous studies have attempted to discern biofluid metabolites consistent with an 'in vivo' whole-body response to radiation using laboratory rodents, specifically blood and urine. All studies published related to analyses of the former confirm differences in metabolites in response to ionizing radiation, albeit with little concordance. Urine has been a particular focus, as metabolites are expected to accumulate in the bladder and thus can be pooled and collected over set time periods. In one series of studies, urine was collected from male C57BL6 mice 24 hours after being irradiated between 0 and 8 Gy, and was subsequently analyzed for metabolite markers for radiation injury [4,5]. These studies indicated that the the pyrimidine and purine metabolic pathway compounds thymidine, deoxyuridine and deoxyxanthosine were consistent markers for radiation exposure—however these authors noted that the response of these markers saturated beyond 3 Gy. Such saturation was also reported for the urinary derived pyrimidine deoxycytidine [6]. Subsequent studies using Wistar rats using a sham versus 3Gy whole body irradiation indicated a common upregulated pyrimidine response associated with excess thymidine, a likely consequence of increased DNA breakdown and cell turnover after exposure to irradiation [7,8]. This issue of 'saturation' is however a cause for some concern from a diagnostic perspective.

Whilst there has been less focus on blood plasma metabolomics, prior studies have indicated that the presence of specific metabolites and proteins in serum/plasma are indicators of radiation exposure, namely citrulline (epithelial radiation-induced small bowel damage) [9], amylase (radiation damage to the parotid gland) [10] and Flt3-ligand (bone marrow radiation damage) [11]. All three are associated with a specific point of origin and whilst they may be broadly used to confirm significant radiation exposure, they do so without any great specificity [12]. Furthermore, in each case there is no data articulating the dynamic range, both in time and in metabolite concentration, with regard to received radiation dose, making it difficult to use these as suitably robust biomarkers.

There have been limited studies to date characterizing serum/plasma metabolomics' response to ionizing radiation as a function of varying dose and time after irradiation. Using proton nuclear magnetic resonance spectroscopy (1H NMR), Khan et al. [13] studied the serum metabolites of groups of irradiated mice exposed to 3, 5, and 8 Gy respectively, with serum obtained day 1, 3, and 5 post-irradiation. These authors reported results showing increased lactate, amino acids, choline, and lipid signals as well as decreased glucose signals. Although it is difficult to absolutely quantify 1H NMR spectra, these authors did not report any saturation in the serum metabolite signals identified beyond the 3 Gy level.

A subsequent publication by the same group obtained serum and urine from a single cohort of the same mice strain, exposed to 5 Gy [14]. Samples were taken at time points designed to best reflect the phases of radiation sickness (6 h, 5 days, 10 days, 15 days, 20, and 25 days post-irradiation), and subjected to 1H NMR. This data confirmed the serum observations made in their earlier publication, but also strongly implicated the presence of a gastrointestinal component in the urine metabonome, with increased trimethyl amine, hippurate, phenylalanine, and other aromatic amino acid signals. In [15], sham and 6.5 Gy irradiated Wistar rats had their blood plasma analyzed using liquid chromatography-mass spectrometry at 24 hours post-exposure. 19 metabolites were identified as associated with a broad range of metabolic pathways, including both pyrimidine and tryptophan—the latter again associated with a gastrointestinal origin.

Perturbations to the gut microbiome—by the use of germ-free or antibiotic treated mice—have been known for some time to profoundly alter the blood metabolite content, most particularly those pathways associated with aromatic amino acids. Indeed, the production of bioactive indole-containing metabolites derived from tryptophan is totally dependent on the gut microbiome [16]. The evidence from the literature to date suggests that there are in fact two convolved signals in both urine and in blood plasma associated with a whole body response to irradiation, one from the host and the second from its symbiont, the gut microbiome. This suggests that the latter undergoes some form of metabolic dysbiosis itself in response to radiation injury, presenting the possibility that its characterization could offer an alternative and promising route to radiation injury biomarkers. Furthermore, the gut microflora impacts crypt loss and survival of mice exposed to whole body irradiation [17,18].

Assessing whole-body radiation injury and absorbed dose is essential for remediation efforts following accidental or deliberate exposure in medical, industrial, military, or terrorist incidents.

The present invention addresses the need for the ability to easily determine the radiation dose that a subject has been exposed to.

SUMMARY OF THE INVENTION

A kit is provided for determining the dose of radiation that a subject has been exposed to, the kit comprising:
a mass spectrometer;
a receptacle into which a body fluid sample from the subject is placed, and which is connected to the mass spectrometer so that the mass spectrometer can measure a plurality of metabolite levels in the sample;
a microprocessor to implement an algorithm on data comprising the plurality of metabolite levels in the sample so as to determine the dose of radiation that the subject has been exposed to;
a visual display and/or audible signal that indicates the dose of radiation that the subject has been exposed to.

Also provided is a method of determining the dose of radiation that a subject has been exposed to, comprising:
a) quantifying the level of a plurality of metabolites in a sample obtained from a subject;
b) implementing an algorithm on data comprising the quantified plurality of metabolite levels so as to obtain an algorithm output;
c) determining the dose of radiation that the subject has been exposed to from the algorithm output of step b).

Also provided is a system comprising:
one or more data processing apparatus; and
a non-transitory computer-readable medium coupled to the one or more data processing apparatus having instructions stored thereon which, when executed by the one or more data processing apparatus, cause the one or more data processing apparatus to perform a method for determining the dose of radiation that a subject has been exposed to, comprising:
a) quantifying the level of a plurality of metabolites in a sample obtained from a subject;
b) implementing an algorithm on data comprising the quantified plurality of metabolite levels so as to obtain an algorithm output;
c) determining the dose of radiation that the subject has been exposed to from the algorithm output of step b).

DETAILED DESCRIPTION OF THE INVENTION

Figure 1:
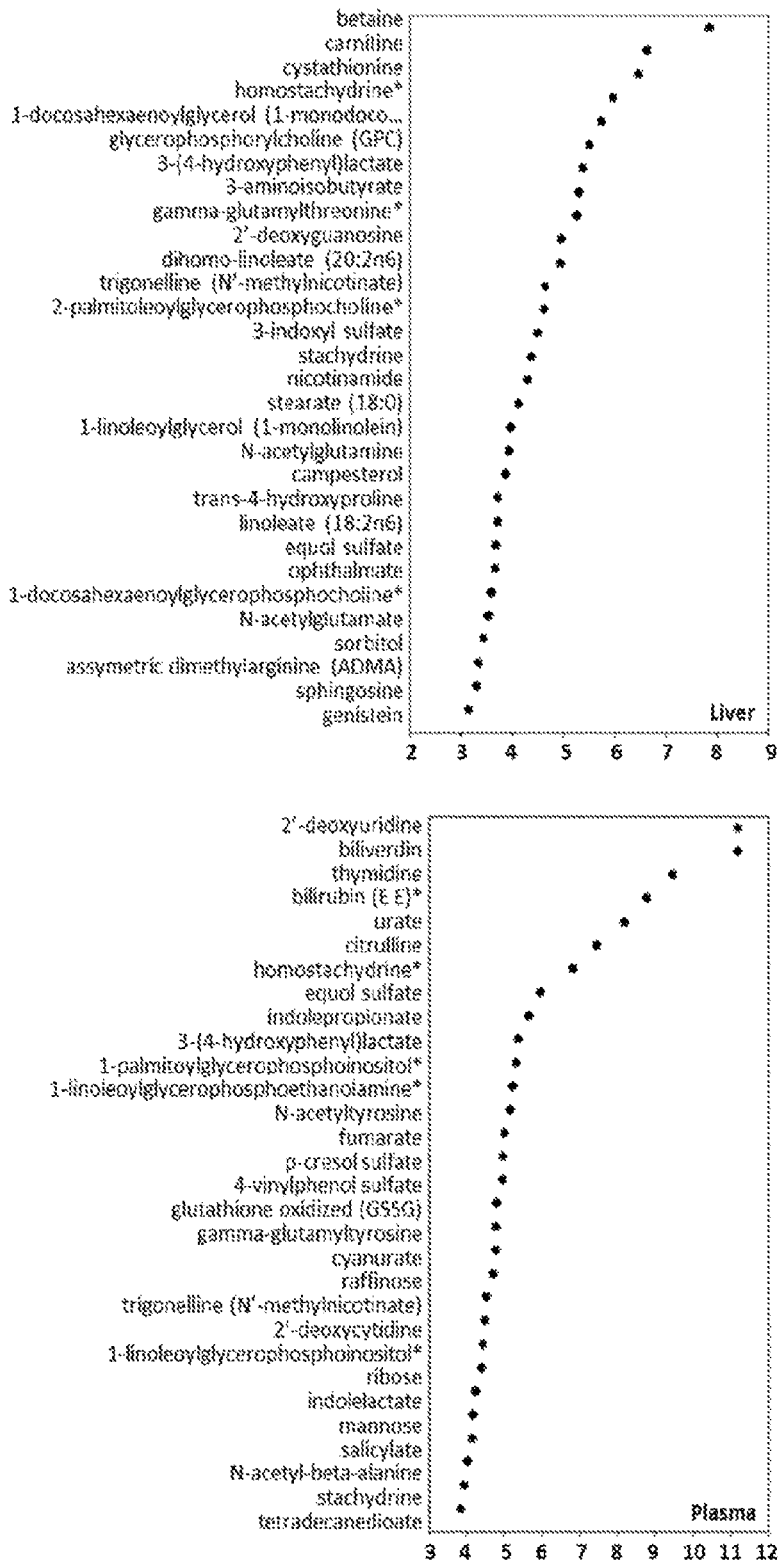
FIG. 1. Random Forest classification analysis of liver samples (left) and plasma samples (right). In both cases the list of biochemicals associated with group separation increase along the y-axis, with the x-axis representing the mean decrease in accuracy (MDA).

A kit is provided for determining the dose of radiation that a subject has been exposed to, the kit comprising:
a mass spectrometer;
a receptacle into which a body fluid sample from the subject is placed, and which is connectable to the mass spectrometer so that the mass spectrometer can measure a plurality of metabolite levels in the sample;
a microprocessor to implement an algorithm on data comprising the plurality of metabolite levels in the sample so as to determine the dose of radiation that the subject has been exposed to;
a visual display and/or audible signal that indicates the dose of radiation that the subject has been exposed to.

In an embodiment, the kit further comprises written instructions for use thereof. In an embodiment, the receptacle into which a body fluid sample from the subject is placed is connected to the mass spectrometer.

In an embodiment, the plurality of metabolites comprise metabolites arising from both the subject and from the intestinal microbiota of the subject. In an embodiment, the plurality of metabolites comprises 10 or more of the following metabolites:
Thymidine
2'-Deoxyuridine
2-Aminobutyrate
2-Hydroxyisobutyrate
1-Eicosadienoylglycerophosphocholine
2-Palmitoylglycerophosphocholine
Ectoine
Homocitrulline
3-Hydroxypropanoate
Citrulline
1-Arachidonoylglycerophosphoethanolamine
Equol glucuronide
3-Phenylpropionate (hydrocinnamate)
Stachydrine
1-Palmitoleoylglycerophosphocholine
*chiro*-Inositol
Docosahexaenoate (DHA22:6n3)
gamma-Glutamylisoleucine 1-Arachidonoylglycerophosphoinositol
Eicosapentaenoate (EPA20:5n3)
Pipecolate
Dihomo-linolenate (20:3n3 or n6)
1-Myristoylglycerophosphocholine
2-Linoleoylglycerophosphoethanolamine
Salicylate
Phenol sulfate
N-acetylhistidine
4-Vinylphenol sulfate
1-Linoleoylglycerophosphoethanolamine
3-Indoxyl sulfate
p-Cresol sulfate
Indolelactate
1-Linoleoylglycerophosphoinositol
Homostachydrine
1-Palmitoylglycerophosphoinositol
Equol sulfate
Indolepropionate.

In an embodiment, the plurality of metabolites comprises 20 or more the listed metabolites. In an embodiment, the plurality of metabolites comprises 30 or more the listed metabolites. In an embodiment, the plurality of metabolites comprises all 37 of the listed metabolites.

In an embodiment, the body fluid sample is a blood sample, blood derivative or blood plasma.

In an embodiment, the subject is a human subject.

Also provided is a method of determining the dose of radiation that a subject has been exposed to, comprising:
a) quantifying the level of a plurality of metabolites in a sample obtained from a subject;
b) implementing an algorithm on data comprising the plurality of quantified metabolite levels so as to obtain an algorithm output;
c) determining the dose of radiation that the subject has been exposed to from the algorithm output of step b).

In an embodiment, the method employs a kit as described herein. In an embodiment, the plurality of metabolites comprise metabolites arising from both the subject and from the intestinal microbiota of the subject.

In an embodiment, the plurality of metabolites comprise 10 or more of the following metabolites:
Thymidine
2'-Deoxyuridine
2-Aminobutyrate
2-Hydroxyisobutyrate
1-Eicosadienoylglycerophosphocholine
2-Palmitoylglycerophosphocholine
Ectoine
Homocitrulline
3-Hydroxypropanoate
Citrulline
1-Arachidonoylglycerophosphoethanolamine
Equol glucuronide
3-Phenylpropionate (hydrocinnamate)
Stachydrine
1-Palmitoleoylglycerophosphocholine
chiro-Inositol
Docosahexaenoate (DHA22:6n3)
gamma-Glutamylisoleucine
1-Arachidonoylglycerophosphoinositol
Eicosapentaenoate (EPA20:5n3)
Pipecolate
Dihomo-linolenate (20:3n3 or n6)
1-Myristoylglycerophosphocholine
2-Linoleoylglycerophosphoethanolamine
Salicylate
Phenol sulfate
N-acetylhistidine
4-Vinylphenol sulfate
1-Linoleoylglycerophosphoethanolamine
3-Indoxyl sulfate
p-Cresol sulfate
Indolelactate
1-Linoleoylglycerophosphoinositol
Homostachydrine
1-Palmitoylglycerophosphoinositol
Equol sulfate
Indolepropionate.

In an embodiment, the plurality of metabolites comprise 20 or more the listed metabolites. In an embodiment, the plurality of metabolites comprise 30 or more the listed metabolites. In an embodiment, the plurality of metabolites comprise all 37 of the listed metabolites.

In an embodiment, the body fluid sample is blood sample, blood derivative or blood plasma.

In an embodiment, the dose of radiation that the subject has been exposed to is determined to be 1 to 2 Gy; 2 to 4 Gy; 4 to 6 Gy; 6 to 8 Gy; or in excess of 8 Gy.

In an embodiment, the method is performed within 24 hours after exposure of the subject to the radiation dose. In an embodiment, the method is performed within 48 hours after exposure of the subject to the radiation dose. In an embodiment, the method is performed within 72 hours after exposure of the subject to the radiation dose.

In an embodiment, the method further comprises treating the subject with a therapy proportionate to the dose of radiation the subject has been determined to have been exposed to.

In an embodiment, the method further comprises quantifying the level of each of the plurality of metabolites using a mass spectrometer.

In a preferred embodiment, the algorithm used is the 'sparse Partial Least Squares-Discriminant Analysis," or "sPLS-DA." The algorithm is freely available through the R statistical computing environment as part of the 'mixOmics' package. Such an algorithm is also available on the world-wide web at CRAN.R-project.org/package=mixOmics.

In an embodiment, the model's predictive ability was assessed using leave-one-out cross validation. Thus, for each of the samples:
1) a model was trained on all other samples except the selected one;
2) the left out sample was assigned a radiation dosage by the trained model based on its metabolite levels. In experiments, the assigned dosage was then compared to the actual dosage. 68% fidelity was observed.

Embodiments of the invention and all of the functional operations described in this specification can be implemented in digital electronic circuitry, or in computer software, firmware, or hardware, or in combinations of one or more of them. Embodiments of the invention can be implemented as one or more computer program products, i.e., one or more modules of computer program instructions encoded on a computer readable medium for execution by, or to control the operation of, data processing apparatus. The computer readable medium can be a machine readable storage device, a machine readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

Also provided is a system comprising:
one or more data processing apparatus; and
a non-transitory computer-readable medium coupled to the one or more data processing apparatus having instructions stored thereon which, when executed by the one or more data processing apparatus, cause the one or more data processing apparatus to perform a method for determining the dose of radiation that a subject has been exposed to, comprising:
a) quantifying the level of a plurality of metabolites in a sample obtained from a subject;
b) implementing an algorithm on data comprising the quantified plurality of metabolite levels so as to obtain an algorithm output;
c) determining the dose of radiation that the subject has been exposed to from the algorithm output of step b).

In an embodiment, the plurality of metabolites comprise metabolites arising from both the subject and from the intestinal microbiota of the subject. In an embodiment, the plurality of metabolites comprise 10 or more of the following metabolites:
Thymidine
2'-Deoxyuridine
2-Aminobutyrate
2-Hydroxyisobutyrate
1-Eicosadienoylglycerophosphocholine
2-Palmitoylglycerophosphocholine
Ectoine
Homocitrulline
3-Hydroxypropanoate
Citrulline
1-Arachidonoylglycerophosphoethanolamine
Equol glucuronide
3-Phenylpropionate (hydrocinnamate)
Stachydrine
1-Palmitoleoylglycerophosphocholine
*chiro*-Inositol
Docosahexaenoate (DHA22:6n3)
gamma-Glutamylisoleucine
1-Arachidonoylglycerophosphoinositol
Eicosapentaenoate (EPA20:5n3)
Pipecolate
Dihomo-linolenate (20:3n3 or n6)
1-Myristoylglycerophosphocholine
2-Linoleoylglycerophosphoethanolamine
Salicylate
Phenol sulfate
N-acetylhistidine
4-Vinylphenol sulfate
1-Linoleoylglycerophosphoethanolamine
3-Indoxyl sulfate
p-Cresol sulfate
Indolelactate
1-Linoleoylglycerophosphoinositol
Homostachydrine
1-Palmitoylglycerophosphoinositol
Equol sulfate
Indolepropionate.

In an embodiment, the plurality of metabolites comprise 20 or more the listed metabolites. In an embodiment, the plurality of metabolites comprise 30 or more the listed metabolites. In an embodiment, the plurality of metabolites comprise all 37 of the listed metabolites. In an embodiment, the body fluid sample is blood sample, blood derivative or blood plasma. In an embodiment, the levels of metabolites are quantified using a mass spectrometer and the mass spectrometer is functionally coupled to the data processing apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows (e.g. for algorithms) described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the invention can be implemented on a computer having a display device, e.g., in non-limiting examples, a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

The computer-readable media as used herein are non-transitory, i.e. not a transitory, propagating signal.

In an embodiment of the inventions described herein, the mass spectrometer is part of a gas chromatography mass spectrometer system. In an embodiment of the inventions described herein, the mass spectrometer is part of a liquid chromatography mass spectrometer system.

In an embodiment, "determining" as used herein means experimentally determining.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Disclosed herein is a clear gut microbiome signature in an untargeted metabolomics screen of C57BL/6 murine liver and blood plasma samples taken 24 hours post-irradiation from groups of 12 animals exposed to sham (0, 2, 4, 8, 10.4 Gy) doses corresponding to different severities of ARS as determined by the IAEA and WHO: mild (1-2 Gy), moderate (2-4 Gy), severe (4-6 Gy), very severe (6-8 Gy), lethal (>8 Gy). The possibility of "saturation signatures," previously reported in several urine studies, were also investigated present in the serum samples. The extracted samples were split into equal parts for processing on both GC/MS and LC/MS/MS platforms (Metabolon, Inc.), with the data processed using Metabolon standard analysis workflows. A total of 354 metabolites/lipids were identified, which were subsequently independently reanalyzed using in-house bioinformatics.

Materials and Methods

Five groups of 12 male C57BL/6 mice were used in this study, each group member receiving a whole-body dose of 0, 2, 4, 8, or 10.4 Gy. Whole-body irradiation (WBI) was performed on anesthetized mice (intraperitoneal ketamine and xylazine 7:1 mg/ml for 100 ml/mouse) using a Shepherd[137]Cs-ray irradiator at a dose rate of 236cGy/min (see Table 1 for details). Liver and plasma samples were collected at 24 hours, ad-lib, after the 0 Gy, sham treatment, or whole-body irradiation, and snap frozen at −80° C. All samples were then sent to Metabolon, Inc. (Durham, N.C.) for processing. A second cohort of C57BL/6 mice (n=6 per group) were used to assess response in selected plasma biomarkers at 48 and 96 hours post-irradiation.

Liver Biomarkers: For the liver samples, random forest analysis was used to classify the sham (0 Gy) and radiation-exposed groups with a predictive accuracy of 45%, with evidence of biochemicals involved in amino acid metabolism, lipid metabolism and nucleotide metabolism varying in response to radiation dose (FIG. 1). Linear discriminant analysis (LDA) showed limited separation of the dose cohorts with a predictive accuracy of 38% against sham (0 Gy). Principal component analysis failed to differentiate all 5 groups. Examination of individual biochemicals showed significant elevations in essential and long-chain fatty acids were observed in mice exposed to the highest dose of radiation (10.4 Gy), likely a consequence of increased lipolysis, and reduced glutathione in the non-sham groups was attributed to increased glutathione synthesis, consistent with a quenching of reactive oxygen species (ROS) in response to radiation. The same dataset was subjected to sparse partial least squares-discriminant analysis (sPLS-DA) [19] to the bounding 10.4 Gy vs. 0 Gy liver samples. Using this independent technique it was confirmed there was a clear separation between sample groups, with all of the key metabolites differentiating the groups identical to those determined by the random forest analysis.

Plasma Biomarkers: Random forest analysis achieved a predictive accuracy of 61% when classifying the sham (0 Gy) and radiation-exposed groups (FIG. 1). The top 30 ranking biochemicals indicated important roles for nucleotide metabolism, amino acid metabolism and lipid metabolism. Linear discriminant analysis clearly segmented the sham (0 Gy) groups from the irradiated groups, although the latter lost their group identity—the overall predictive accuracy using this technique gave an accuracy of 36%. Principal component analysis failed to separate all but a subset of the 10.4 Gy group. Individual examination of biochemicals showed evidence for perturbations in pyrimidine metabolism, degradation of heme and more generally, alterations in lipid metabolism and tryptophan metabolism. In particular, stepwise changes in thymidine and 2-deoxyuridine for pyrimidine metabolism, biliverdin and bilirubin for heme degradation, certain fatty acids (lipid metabolism) and aromatic amino acids (tryptophan metabolism) were evident. The latter metabolites were of some interest, as these aromatic amino acids have been shown to have their origin within the intestinal microbiome [16,20].

Figure 2:
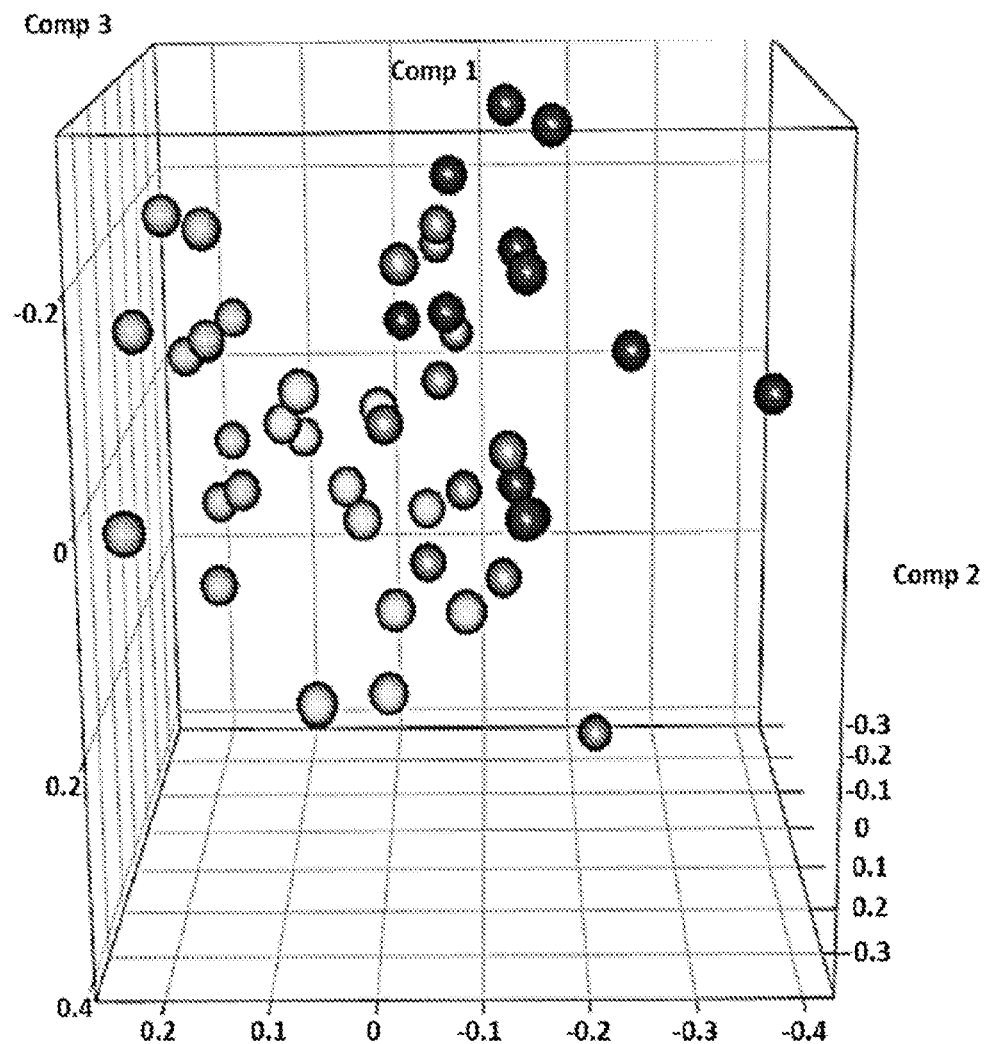
FIG. 2. All the plasma sample groups have been projected/clustered based on the multidimensional space defined by the best sPLS-DA model determined from the 37 biochemical compounds listed in Table 1. Note that only the first three components are shown, but these are the ones capturing the most variance in the dataset. The samples are colored as follows: Green-0 Gy, Yellow-2 Gy, Orange-8 Gy, Red-10.4 Gy.

An independent, unsupervised analysis was implemented based around an attempt to discern a cohort of metabolites and lipids whose level of increase/decrease was consistently correlated with radiation dose. Given the full dataset we (i) used the Pearson correlation coefficient (PCC) to determine biochemicals which showed either a positive or negative correlation with increased dosage, selecting those with an absolute correlation value ≥0.45; (ii) the resulting 37 metabolites (Table 2) were analyzed using sPLS-DA; (iii) models with up to 10 components containing subsets of 5, 10, 15, 20, 25, 30, or 35 metabolites on each component were generated and leave one out cross-validation (LOOCV) was used to choose the best model (i.e. number of components and metabolites giving the lowest predictive error rate). This analysis was repeated by removing each of the non-boundary radiation groups and noted that excluding the 4 Gy group yielded more optimal correlation scores and overall predictive accuracy. The lowest error rate was achieved using a model with 5 components and selecting 5 metabolites on each of these components. The overall error rate for this model was 0.32, representing a 68% accuracy in predicting dosage—as distinct from the 61% classification estimate determined from the random forest classifier for 0 Gy versus all irradiated groups combined. In FIG. 2 it is shown how the samples are projected/clustered based on the multidimensional space defined by this model. Note that only the first three components are shown, but these are the ones capturing the most variance in the dataset. Not only are the irradiated groups clearly separable, but also their contiguous separation along the first component correlates with increasing radiation dose. Whilst there was general agreement between the random forest derived top ranked biochemicals and those determined from our sPLS-DA analysis, the correspondence of these 37 metabolites and increased radiation dose gives us a tractable cohort of potential biomarkers with which to not only to validate, but also to form the basis of a plasma-based metabolite panel for radiation dose estimation.

Figure 3:
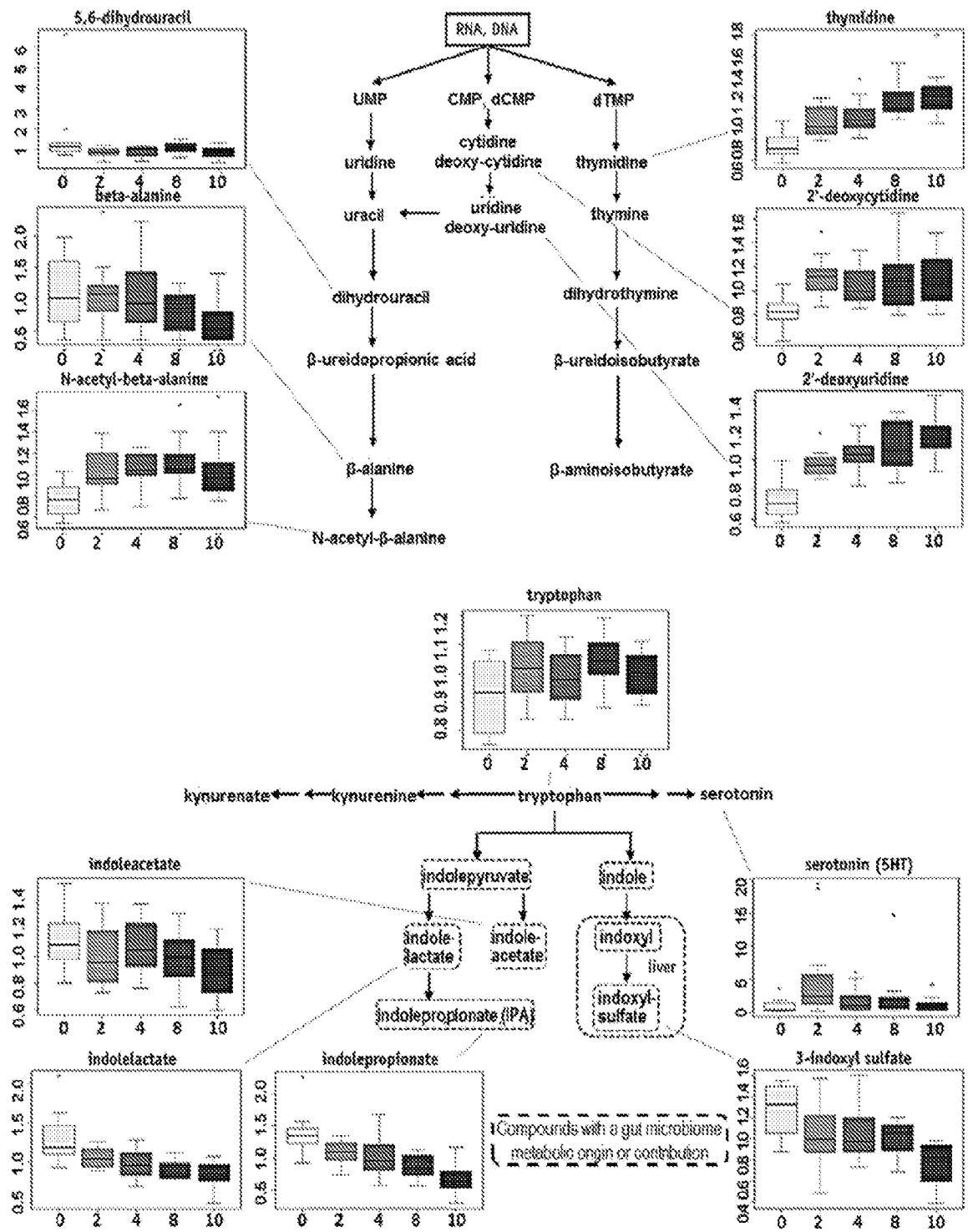
FIG. 3. Pyrimidine (upper panel) and tryptophan (lower panel) metabolism pathways and associated metabolite measurements in plasma. The x-axis indicates received radiation dosage in Gy.

Plasma Microbiome Signature: Of the biochemicals that significantly correlated with radiation dose, those that increased (thymidine and 2-deoxyuridine) recapitulated those identified in the context of pyrimidine metabolism (FIG. 3, upper panel), and of those that decreased (<−0.55), four biochemicals in particular (indolepropionate, equol sulfate, indole lactate and 3-indoxyl sulfate) are all tryptophan compounds with a gut microbiome metabolic contribution (FIG. 3, lower panel). Thus it seems clear that the predominant metabolite components of the plasma response to enhanced irradiation are those associated with DNA strand breaks/RNA damage (increases with irradiated dose) and those metabolites originating or associated directly with the gut microbiome (decreases with irradiated dose).

Figure 4:
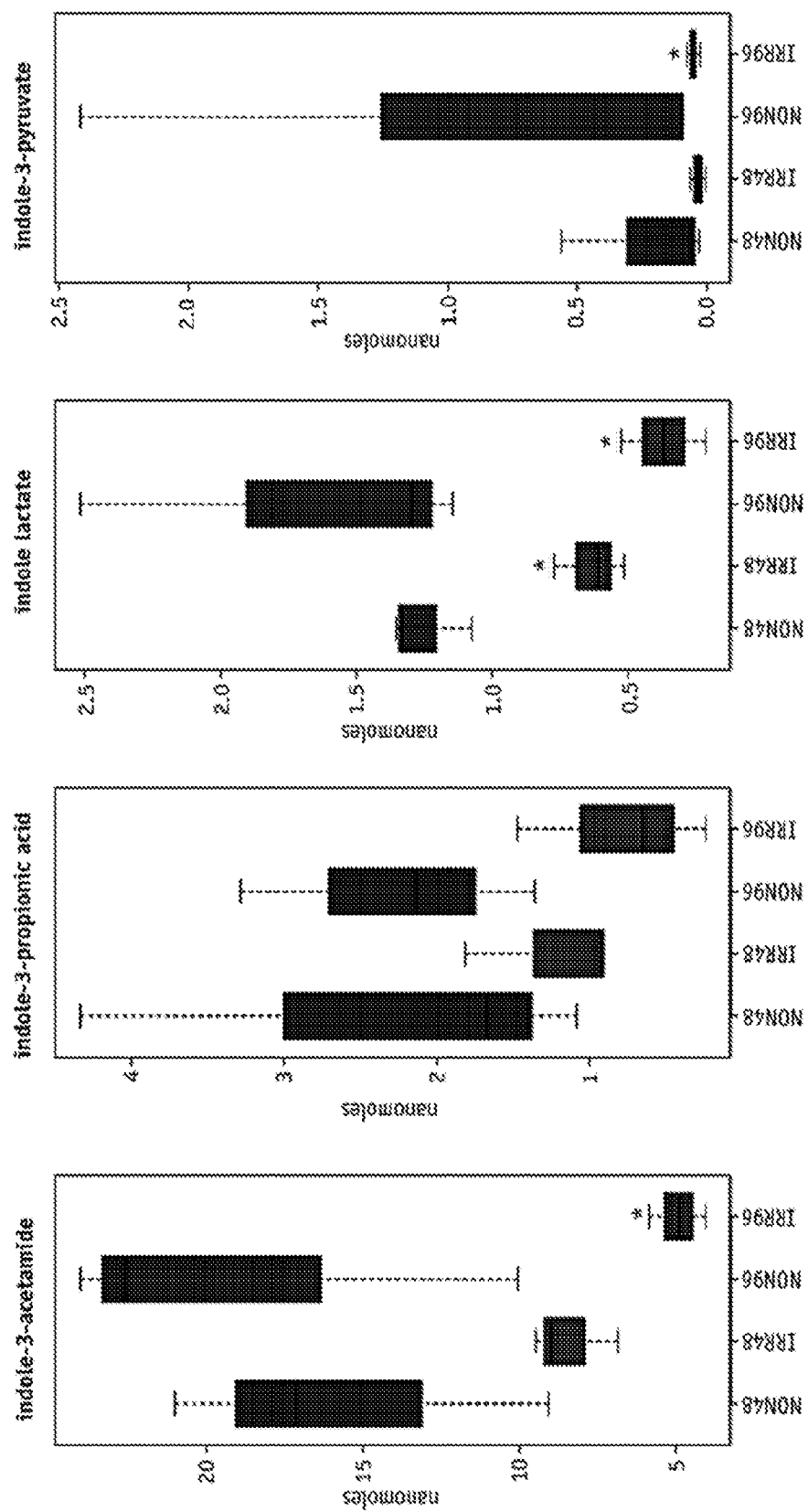
FIG. 4. Indole metabolites measured in a second cohort of mice receiving 10.4 Gy show persistent changes at both 48 (IRR48) and 96 (IRR96) hours post-irradiation compared to their respective non-irradiated counterparts (NON48 and NON96). Asterisks identify significantly changed metabolites ($p<=0.1$) between irradiated samples and controls at each timepoint using a non-parametric Wilcoxon rank-sum test.

Plasma Response beyond 24 hours: To further assess this gut microbiome response, a second cohort of male C57BL/6 mice were used to validate a subset of the identified biomarkers and to examine their behavior in the ad-lib state beyond 24 hours post-irradiation. In this second experiment, selected markers were measured at either 48 or 96 hours post-irradiation in groups (n=6 per group) of mice receiving a 10.4 Gy radiation dose as compared to non-irradiated controls (FIG. 4). Results from this experiment show that indole-3-pyruvate and indole-3-acetamide are also detected as being markedly reduced in irradiated samples along with the previously identified biomarkers IPA and indole lactate and that decreases in indole levels are evident at both timepoints, indicating persistent changes in tryptophan metabolism.

Correlation between Liver and Plasma: whether there was a common metabolite/lipid association between the liver and plasma was investigated—choosing the boundary 0 Gy and 10.4 Gy groups to perform this analysis so as to best emphasize any correlated signal across the two profiles. The highest scoring biochemical, common to both liver and plasma datasets was 3-indoxyl sulfate, a sulfated gut microbiome metabolite of tryptophan processed in the liver.

Preparation of Plasma and Liver Samples: The MicroLab STAR® system from Hamilton Company was used to prepare the plasma and liver samples. Solvent extraction was implemented with spike-in recovery standards for QC purposes, placed briefly on a TuboVap® (Zymark) to remove the organic solvent, then frozen into two batches, for analysis on the GC/MS (Thermo-Finnigan Trace DSQ) and LC/MS (Surveyor HPLC coupled to an LTQ mass spectrometer, Thermo-Finnigan). Also included were several technical replicate samples created from a homogeneous pool containing a small amount of all study samples.

Gas chromatography/Mass Spectroscopy (GC/MS): Samples were prepared under vacuum desiccation for a minimum of 24 hours prior to being derivatized in dried nitrogen using bistrimethyl-silyl-triflouroacetamide (BSTFA). The GC column was 5% phenyl and the temperature ramp is from 40° C. to 300° C. in a 16-minute period. Samples were analyzed on a Thermo-Finnigan Trace DSQ single-quadrupole mass spectrometer using electron impact ionization. The instrument was tuned and calibrated for mass resolution and mass accuracy on a daily basis.

Liquid chromatography/Mass Spectrometry (LC/MS): Each sample extract was split into two aliquots, dried, and then reconstituted in acidic or basic LC compatible solvents, each of which contained 11 or more injection standards at fixed concentrations. One aliquot was analyzed using acidic positive ion optimized conditions and the other using basic negative ion optimized conditions in two independent injections using separate dedicated columns. Extracts reconstituted in acidic conditions were gradient eluted using water and methanol both containing 0.1% Formic acid, while the basic extracts, which also used water/methanol, contained 6.5 mM Ammonium Bicarbonate. The LC/MS component used is based on a Surveyor HPLC and a Thermo-Finnigan LTQ mass spectrometer Positive and negative ions were monitored within a single analysis by consecutively alternating the ionization polarity of adjacent scans. The vacuum-dried sample was dissolved in 100.0 µl of an injection solvent that contained five or more injection standards at fixed concentrations. The chromatographic system used a binary solvent system delivered as a gradient. Solvent A was water and solvent B was methanol. Both were high purity grade and both contained 0.1% formic acid as a pH stabilizer. The HPLC columns were washed and reconditioned after every injection.

Exact mass determinations were performed using a Thermo-Finnigan LTQ-FT mass spectrometer, which had a linear ion-trap (LIT) front end and a Fourier transform ion cyclotron resonance (FT-ICR) mass spectrometer backend. For ions with counts greater than 2 million, an accurate mass measurement could be performed. Accurate mass measurements could be made on the parent ion as well as fragments. The typical mass error was less than 5 ppm. Ions with less than two million counts require a greater amount of effort to characterize. Fragmentation spectra (MS/MS) were typically generated in data dependent manner, but if necessary, targeted MS/MS could be employed, such as in the case of lower level signals.

Mass Spectrometry Data Extraction and Peak Identification: All data generated by the various mass spectrometry platforms were loaded into a database server running Oracle 10.2.0.1 Enterprise Edition, from where they where subsequently processed. The QC and curation processes were implemented to ensure accurate and consistent identification of true chemical entities, and to remove those representing system artifacts, mis-assignments, and background noise. Peaks were identified using Metabolon's peak integration software. Compounds were identified by comparison to library entries of purified standards or recurrent unknown entities. Library matches for each compound were checked for each sample and corrected if necessary. For studies spanning multiple days, a data normalization step was performed to correct variation resulting from instrument interday tuning differences. Each compound was corrected in runday blocks by registering the medians to equal one (1.00) and normalizing each data point proportionately.

Data Analysis and Identification of Radiation Response Biomarkers: To facilitate visualization of fold changes, all data were normalized to a mean value of 1 for sham-operated (0 Gy-treated) animals. For pair-wise comparisons, Welch's t-tests and/or Wilcoxon's rank sum tests were used. For classification a random forest analysis was used which is an ensemble decision tree approach. Briefly, for a given decision tree, a random subset of the data with identifying true class information is selected to build the tree ("bootstrap sample" or "training set"), and then the remaining data, the "out-of-bag" (OOB) variables, are passed down the tree to obtain a class prediction for each sample. This process is repeated thousands of times to produce the forest. The final classification of each sample is determined by computing the class prediction frequency for the OOB variables over the whole forest. The "Mean Decrease Accuracy" (MDA) is determined by randomly permuting a variable and then reassessing the prediction accuracy, if the variable is important to the classification, the prediction accuracy will drop after such a permutation. To determine correlations between metabolite relative concentrations as a function of radiation dose, Pearson and Spearman correlation measures were used. The algorithm used was the 'sparse Partial Least Squares-Discriminant Analysis," or "sPLS-DA." The algorithm is freely available through the R statistical computing environment as part of the 'mixOmics' package. Such an algorithm is also available on the worldwide web at CRAN.R-project.org/package=mixOmics.

In an embodiment, the model's predictive ability was assessed using leave-one-out cross validation. Thus, for each of the samples:
1) a model was trained on all other samples except the selected one;
2) the left out sample was assigned a radiation dosage by the trained model based on its metabolite levels. In experiments, the assigned dosage was then compared to the actual dosage. 68% fidelity was observed.

All statistical analyses were performed within the R statistical processing environment.

Validation Samples: Fifty-100 µl blood plasma was spiked with 10 nmoles of U-13C succinate, D5 trypotophan as internal standard, deproteinized, extracted and was dried under nitrogen. The dried residue was derivatised with Bis (Trimethylsilyl) trifluoroacetamide (BSTFA) containing 10% trimethyl chlorosilane (TMCS) and analysed on GCMS as trimethyl silyl (TMS) derivatives. The TMS derivatives of indole compounds were was isolated on an DB-17MS capillary column, 30 m 250 µm internal diameter. GC conditions were helium as carrier gas at a flow rate of 1.0 ml/min, and sample injector temperature of 250° C. Selective Ion monitoring (SIM) was performed on a Hewlett-PackardMass Selective Detector (model 7890A, Hewlett-Packard, Palo Alto, Calif.) connected to a Hewlett-Packard gas chromatograph (model 5975c) using electron impact (EI) ionization. Ions monitored were m/z 251 for U-13C succinate, m/z 202,319 for Indole acetate, m/z 202 and 333 for Indole propionate, m/z 202 and 421 for Indole lactate, 202 for tryptophan, and 207 for D5 tryptophan.

Discussion

The purpose of this work was to determine if consistent trends in metabolite and lipid concentrations were discernible in blood plasma taken from whole body irradiated mice 24 hours after a range of doses equivalent to non-lethal, sub-lethal and lethal exposures. We included liver samples as liver is a prime indicator for the radiation response, due to the effects of radiation on mitochondrial oxidative metabolism and antioxidant defenses in response to acute radiation-induced liver injury. The lack of a discernable response in liver samples below 10.4 Gy indicates that these anti-oxidant defenses are largely effective in dealing with perturbations to the normal metabolite profile caused by ionizing radiation. Whilst it was difficult to identify a coherent set of biomarkers for murine hepatic response to radiation, we were able to do so for extracted blood plasma. Of the 37 biochemicals whose concentrations were correlated to radiation dose, the dominant underlying metabolic pathways were those associated with pyrimidine and tryptophan metabolism. Whilst the presence of metabolite compounds associated with these two pathways is in agreement with several previous irradiation studies, our work is the first to indicate their concentration being consistently correlated with received dose. We did not see evidence for a dose-response saturation as reported by previous studies on urine derived metabolites—this serves to highlight the potential advantage in using plasma as a biofluid for such functional biodosimetry studies. Of particular interest is the extent to which we can implicate a predominantly microbiome signature evident in murine plasma in the form of several of the indole family of biochemical compounds, whose presence is inversely correlated with radiation dose from 0 Gy to 10.4 Gy. In addition we see a similar correlation between plasma and liver for 3-indoxyl sulfate, which is a by-product of hepatic processing of indole, between 0 and 10.4 Gy.

Whilst the intestinal microbial response to ionizing radiation has not been formally determined, the study of ionizing radiation on individual prokaryotes has typically focused on model strains (most notably E. coli), in isolation and under controlled conditions. Inhibition of tryptophanase, the engine of tryptophan metabolism, has been reported in the literature [21], but involved doses ≥103 Gy and was quantified very shortly after radiation exposure, where the presence of significant numbers of both single and double strand breaks might be expected to compromise the conventional prokaryotic transcriptome. Clearly the radiation dosage in the whole body context is unlikely to yield such a profound transcriptional response. Assuming that the colonic microbiome is in effect transcriptionally unperturbed by increased radiation doses within the range [2-10 Gy], a possible explanation could be that radiation causes damage to the intestinal epithelium, compromising the transfer of indoles and other microbiome metabolites to the host. Indeed, the observed concentration of citrulline in our study is inversely correlated to radiation dose, consistent with damage to the intestinal epithelium. However, such damage is typically associated with an increase in epithelial permeability [22], yet despite this we see a consistent trend for a decrease in indole production. A recent study presented clear evidence for significant microbial dysbiosis in fecal pellets taken from Wistar rats exposed to whole body 10 and 18 Gy doses based on community profiling determined daily over a 21 day period post-irradiation [23].

REFERENCES

1. Stone H B, Coleman C N, Anscher M S, McBride W H. Effects of radiation on normal tissue: Consequences and mechanisms. The lancet oncology 2003; 4:529-536.
2. Friesecke I, Beyrer K, Fliedner T M, system MtMtp-fravaabfacg. How to cope with radiation accidents: The medical management. Br J Radiol 2001; 74:121-122.
3. Fiehn O. Metabolomics—the link between genotypes and phenotypes. Plant molecular biology 2002; 48:155-171.
4. Tyburski J B, Patterson A D, Krausz K W, Slavik J, Fornace A J, Jr., Gonzalez F J, Idle J R. Radiation metabolomics. 1. Identification of minimally invasive urine biomarkers for gamma-radiation exposure in mice. Radiat Res 2008; 170:1-14.
5. Tyburski J B, Patterson A D, Krausz K W, Slavik J, Fornace A J, Jr., Gonzalez F J, Idle J R. Radiation metabolomics. 2. Dose- and time-dependent urinary excretion of deaminated purines and pyrimidines after sublethal gamma-radiation exposure in mice. Radiat Res 2009; 172:42-57.
6. Parizek J, Arient M, Dienstbier Z, Skoda J. Deoxycytidine in urine as an indicator of changes after irradiation. Nature 1958; 182:721-722.
7. Lanz C, Patterson A D, Slavik J, Krausz K W, Ledermann M, Gonzalez F J, Idle J R. Radiation metabolomics. 3. Biomarker discovery in the urine of gamma-irradiated rats using a simplified metabolomics protocol of gas chromatography-mass spectrometry combined with random forests machine learning algorithm. Radiat Res 2009; 172: 198-212.
8. Johnson C H, Patterson A D, Krausz K W, Lanz C, Kang D W, Luecke H, Gonzalez F J, Idle J R. Radiation metabolomics. 4. Uplc-esi-qtofms-based metabolomics for urinary biomarker discovery in gamma-irradiated rats. Radiat Res 2011; 175:473-484.
9. Lutgens L C, Deutz N E, Gueulette J, Cleutjens J P, Berger M P, Wouters B G, von Meyenfeldt M F, Lambin P. Citrulline: A physiologic marker enabling quantitation and monitoring of epithelial radiation-induced small bowel damage. Int J Radiat Oncol Biol Phys 2003; 57:1067-1074.
10. Barrett A, Jacobs A, Kohn J, Raymond J, Powles R L. Changes in serum amylase and its isoenzymes after whole body irradiation. British medical journal 1982; 285:170-171.
11. Bertho J M, Demarquay C, Frick J, Joubert C, Arenales S, Jacquet N, Sorokine-Durm I, Chau Q, Lopez M, Aigueperse J, Gorin N C, Gourmelon P. Level of flt3-ligand in plasma: A possible new bio-indicator for radiation-induced aplasia. Int J Radiat Biol 2001; 77:703-712.
12. Guipaud O. Serum and plasma proteomics and its possible use as detector and predictor of radiation diseases. Adv Exp Med Biol 2013; 990:61-86.
13. Khan A R, Rana P, Devi M M, Chaturvedi S, Javed S, Tripathi R P, Khushu S. Nuclear magnetic resonance spectroscopy-based metabonomic investigation of biochemical effects in serum of gamma-irradiated mice. Int J Radiat Biol 2011; 87:91-97.
14. Khan A R, Rana P, Tyagi R, Kumar I, Devi M M, Javed S, Tripathi R P, Khushu S. Nmr spectroscopy based metabolic profiling of urine and serum for investigation of physiological perturbations during radiation sickness. Metabolomics: Official journal of the Metabolomic Society 2011; 7:583-592.
15. Liu Y, Lin Z, Tan G, Chu Z, Lou Z, Zhang J, Hong Z, Chai Y. Metabonomic studies on potential plasma biomarkers in rats exposed to ionizing radiation and the protective effects of hong shan capsule. Metabolomics: Official journal of the Metabolomic Society 2013; 9:1082-1095.
16. Wikoff W R, Anfora A T, Liu J, Schultz P G, Lesley S A, Peters E C, Siuzdak G. Metabolomics analysis reveals large effects of gut microflora on mammalian blood metabolites. Proc Natl Acad Sci USA 2009; 106:3698-3703.
17. Crawford P A, Gordon J I. Microbial regulation of intestinal radiosensitivity. Proc Natl Acad Sci USA 2005; 102:13254-13259.
18. Onoue M, Uchida K, Yokokura T, Takahashi T, Mutai M. Effect of intestinal microflora on the survival time of mice exposed to lethal whole-body gamma irradiation. Radiat Res 1981; 88:533-541.
19. Le Cao K A, Boitard S, Besse P. Sparse pls discriminant analysis: Biologically relevant feature selection and graphical displays for multiclass problems. BMC bioinformatics 2011; 12:253.
20. Grison S, Martin J C, Grandcolas L, Banzet N, Blanchardon E, Tourlonias E, Defoort C, Fave G, Bott R, Dublineau I, Gourmelon P, Souidi M. The metabolomic approach identifies a biological signature of low-dose chronic exposure to cesium 137. Journal of radiation research 2012; 53:33-43.
21. Pollard E C, Lydersen B K. The action of ionizing radiation on the synthesis of rna and two inducible enzymes in *Escherichia Coli*. Radiat Res 1972; 50:293-300.
22. MacNaughton W K. Review article: New insights into the pathogenesis of radiation-induced intestinal dysfunction. Alimentary pharmacology & therapeutics 2000; 14:523-528.
23. Lam V, Moulder J E, Salzman N H, Dubinsky E A, Andersen G L, Baker J E. Intestinal microbiota as novel biomarkers of prior radiation exposure. Radiat Res 2012; 177:573-583.

What is claimed is:

1. A kit for determining a dose of radiation that a subject has been exposed to, the kit comprising:
a mass spectrometer for quantifying a concentration of each metabolite in a plurality of metabolites;
a receptacle into which a body fluid sample from the subject is placed, and which is connectable to the mass spectrometer so that the mass spectrometer can measure the concentration of each metabolite of the plurality of metabolites in the sample;
a non-transitory computer-readable medium coupled to one or more data processing apparatus having instructions stored thereon which, when executed by the one or more data processing apparatus, cause the one or more data processing apparatus to perform a method for determining the dose of radiation that the subject has been exposed to by implementing an algorithm on a data set comprising the concentration of each metabolite of the plurality of metabolites in the sample so as to determine the dose of radiation that the subject has been exposed to by correlating the concentration of each metabolite of the plurality of metabolites with the received dose of radiation;
a visual display and/or audible signal that indicates the dose of radiation that the subject has been exposed to, wherein the dose of radiation that the subject has been exposed to is determined to be only one of:
1 to 2 Gy;
2 to 4 Gy;
4 to 6 Gy;
6 to 8 Gy;
or greater than 8 Gy, and
wherein the plurality of metabolites consists of:
Thymidine
2'-Deoxyuridine
2-Aminobutyrate
2-Hydroxyisobutyrate
1-Eicosadienoylglycerophosphocholine
2-Palmitoylglycerophosphocholine
Ectoine
Homocitrulline 3-Hydroxypropanoate
Citrulline
1-Arachidonoylglycerophosphoethanolamine
Equol glucuronide
3-Phenyl propionate (hydrocinnamate)
Stachydrine
1-Palm itoleoylglycerophosphocholine
*chiro*-Inositol
Docosahexaenoate (DHA22:6n3)
gamma-Glutamylisoleucine
1-Arachidonoylglycerophosphoinositol
Eicosapentaenoate (EPA20:5n3)
Pipecolate
Dihomo-linolenate (20:3n3 or n6)
1-Myristoylglycerophosphocholine
2-Linoleoylglycerophosphoethanolamine
Salicylate
Phenol sulfate
N-acetylhistidine
4-Vinylphenol sulfate
1-Linoleoylglycerophosphoethanolamine
3-Indoxyl sulfate
p-Cresol sulfate
Indolelactate
1-Linoleoylglycerophosphoinositol
Homostachydrine
1-Palm itoylglycerophosphoinositol
Equol sulfate; and
Indolepropionate.

2. The kit of claim 1, wherein the plurality of metabolites includes metabolites arising from at least one intestinal microbiota within the subject.

3. The kit of claim 1, wherein the body fluid sample is selected from the group consisting of blood, plasma, or another a blood derivative.

4. The kit of claim 1, wherein the subject is a human subject.

5. A method of determining a dose of radiation that a subject has been exposed to, comprising:
  a) quantifying a concentration of each metabolite of a plurality of metabolites in a sample, wherein the sample is selected from the group consisting of blood, plasma, or another a blood derivative;
  b) implementing an algorithm on a data set comprising the quantified concentrations of each metabolite of the plurality of metabolites so as to obtain an algorithm output;
  c) correlating the algorithm output with the dose of radiation that the subject has been exposed to so as to determine the dose of radiation that the subject has been exposed to, wherein the dose of radiation that the subject has been exposed to is only one of
1 to 2 Gy;
2 to 4 Gy;
4 to 6 Gy;
6 to 8 Gy;
or greater than 8 Gy, and
wherein the plurality of metabolites consists of the following metabolites:
Thymidine
2'-Deoxyuridine
2-Aminobutyrate
2-Hydroxyisobutyrate
1-Eicosadienoylglycerophosphocholine
2-Palm itoylglycerophosphocholine
Ectoine
Homocitrulline
3-Hydroxypropanoate
Citrulline
1-Arachidonoylglycerophosphoethanolamine
Equol glucuronide
3-Phenyl propionate (hydrocinnamate)
Stachydrine
1-Palm itoleoylglycerophosphocholine
*chiro*-Inositol
Docosahexaenoate (DHA22:6n3)
gamma-Glutamylisoleucine
1-Arachidonoylglycerophosphoinositol
Eicosapentaenoate (EPA20:5n3)
Pipecolate
Dihomo-linolenate (20:3n3 or n6)
1-Myristoylglycerophosphocholine
2-Linoleoylglycerophosphoethanolamine
Salicylate
Phenol sulfate
N-acetylhistidine
4-Vinylphenol sulfate
1-Linoleoylglycerophosphoethanolamine
3-Indoxyl sulfate
p-Cresol sulfate
Indolelactate
1-Linoleoylglycerophosphoinositol
Homostachydrine
1-Palm itoylglycerophosphoinositol
Equol sulfate; and
Indolepropionate.

6. The method of claim 5, wherein the plurality of metabolites arises from the subject and from at least one intestinal microbiota of the subject.

7. The method of claim 5, wherein the body fluid sample is blood plasma.

8. The method of claim 5, wherein the method is performed within 24 hours after the subject is exposed to the dose of radiation.

9. The method of claim 5, wherein the method is performed within 48 hours after the subject is exposed to the dose of radiation.

10. The method of claim 5, wherein the concentrations of each metabolite of the plurality of metabolites are quantified using a mass spectrometer.

11. A system comprising:
  one or more data processing apparatus; and
  a non-transitory computer-readable medium coupled to the one or more data processing apparatus having instructions stored thereon which, when executed by the one or more data processing apparatus, cause the one or more data processing apparatus to perform a method for determining a dose of radiation that a subject has been exposed to, comprising:
  a) quantifying a concentration of each metabolite in a plurality of metabolites in a sample obtained from the subject, wherein the plurality of metabolites consists of:
Thymidine
2'-Deoxyuridine
2-Aminobutyrate
2-Hydroxyisobutyrate
1-Eicosadienoylglycerophosphocholine
2-Palmitoylglycerophosphocholine
Ectoine
Homocitrulline
3-Hydroxypropanoate
Citrulline
1-Arachidonoylglycerophosphoethanolamine Equol glucuronide
3-Phenyl propionate (hydrocinnamate)
Stachydrine
1-Palmitoleoylglycerophosphocholine
*chiro*-Inositol
Docosahexaenoate (DHA22:6n3)
gamma-Glutamylisoleucine
1-Arachidonoylglycerophosphoinositol
Eicosapentaenoate (EP A20: 5n3)
Pipecolate
Dihomo-linolenate (20:3n3 or n6)
1-Myristoylglycerophosphocholine
2-Linoleoylglycerophosphoethanolamine
Salicylate
Phenol sulfate
N-acetylhistidine
4-Vinylphenol sulfate
1-Linoleoylglycerophosphoethanolamine
3-Indoxyl sulfate
p-Cresol sulfate
Indolelactate
1-Linoleoylglycerophosphoinositol
Homostachydrine
1-Palmitoylglycerophosphoinositol
Equol sulfate
Indolepropionate;

b) implementing an algorithm on a data set that comprises the concentrations of each metabolite in the plurality of metabolites so as to obtain an algorithm output;

c) determining the dose of radiation that the subject has been exposed to after implementing the algorithm output, wherein the dose of radiation that the subject has been exposed to is only one of:

1 to 2 Gy;
2 to 4 Gy;
4 to 6 Gy;
6 to 8 Gy;
or greater than 8 Gy.

* * * * *